United States Patent [19]

Nienow et al.

[11] 4,227,400

[45] Oct. 14, 1980

[54] MEASURING CIGARETTE CHARACTERISTICS DURING PYROLYSIS SMOKING

[75] Inventors: John F. Nienow; Christopher L. Irving; Lynwood V. Shaw, all of Richmond, Va.

[73] Assignee: Philip Morris Incorporated, New York, N.Y.

[21] Appl. No.: 43,454

[22] Filed: May 29, 1979

[51] Int. Cl.³ ............................................. G01N 3/48
[52] U.S. Cl. ......................................... 73/81; 73/796
[58] Field of Search .................. 73/81, 796; 131/21 B

[56] References Cited

U.S. PATENT DOCUMENTS

| | | | |
|---|---|---|---|
| 2,163,415 | 6/1939 | Stephano | 131/21 B |
| 2,338,070 | 12/1943 | Lopez | 73/81 |
| 3,237,764 | 3/1966 | Kochalski et al. | 73/81 |
| 3,368,674 | 2/1968 | Koeppe | 73/81 |
| 3,572,101 | 3/1971 | Moore | 73/81 |

*Primary Examiner*—Donald O. Woodiel
*Attorney, Agent, or Firm*—Watson, Leavenworth, Kelton & Taggart

[57] ABSTRACT

The length and firmness of a cigarette rod during smoking are measured on automatic basis to determine the effects of blend, moisture and temperature on the firmness of a cigarette rod behind the coal of a burning cigarette.

25 Claims, 9 Drawing Figures

ROTARY INDEXING TABLE SCHEMATIC

ROTARY INDEXING TABLE SCHEMATIC

MEASURING CIGARETTE CHARACTERISTICS DURING PYROLYSIS SMOKING

FIELD OF THE INVENTION

The present invention relates to the automatic measurement of cigarette rod firmness and length, and more particularly to the measurement of rod firmness behind the coal of a burning cigarette.

BACKGROUND OF THE INVENTION

Manufacturers of cigarettes have long been desirous of accurately monitoring the firmness of a cigarette rod during making and thereafter for quality control purposes, and such monitoring heretofore has been accomplished in a number of ways. One procedure is that of employing the rod firmness testing apparatus described in U.S. Pat. No. 2,163,415 for detecting rod firmness and used for the purpose of regulating the amount of tobacco entering the machine. U.S. Pat. No. 3,572,101 describes apparatus for measuring the rod firmness of cigarettes after completion. Such methods as well as others known in the cigarette making art deal with measurements made during or after making of the cigarette and generally are carried out under ambient conditions of temperature and humidity. Such testing is not necessarily responsive to changes in cigarette blends and truly reliable as a basis for predicting the expected firmness of a given blend in a cigarette rod during smoking. As a cigarette is smoked and the heated products of combustion are drawn from the coal over the unburned tobacco rod into the smoker's mouth, the action of the heat on the rod of tobacco wets it with the moisture that is formed as a by-product of combustion as well as that moisture which is simply driven off from the tobacco by heat evaporation which occurs adjacent the burning coal. There is also a slight increase in temperature within the tobacco rod due to the passage of the hot smoke therethrough as it travels along the length of tobacco filler from the coal to the smoker's mouth.

A most important aspect of quality with which the manufacturer is concerned, is that feel of a cigarette based on a tobacco blend's characteristics affecting its ability to allow the cigarette to remain firm during smoking. Conventional tests of rod firmness, as they are now made during manufacture in the making equipment, or under laboratory conditions, do not reliably predict the degree of rod firmness to be expected for a given blend during smoking. The testing of rod firmness during smoking introduces effects based upon the above-described changes in the temperature and humidity of the rod which require different treatment in testing. A further set of complexities are introduced as a result of the progressive build-up of moisture to different levels at various points along the shortened rod length during smoking. The increased moisture content builds progressively as the hot smoke conducted through the rod from the combustion zone to the smoker's mouth cumulatively deposits moisture in the tobacco through the condensation of the hot vapors generated near the coal, and the effect of these moisture and temperature changes can be quite different for various tobacco blends.

It is an object of the present invention to provide a method and apparatus to determine in advance the effect that a firmness change due to moisture and heat have on the subjective fingertip impression that is made by a smoker, before lighting and then after several puffs have been taken for cigarettes made with particular blends of tobacco filler.

SUMMARY OF THE INVENTION

The apparatus of the present invention exhibits specific advantages over the prior art in that it automatically feeds, mounts, smokes cigarettes of given blends, and measures the firmness of the cigarettes before they are lit as well as during smoking while the firmness is reflecting the effects of heat, blend and moisture on the tobacco column. It also measures the remaining length of the burning cigarette so as to provide a firmness value for a particular blend for a given length of the cigarette smoked.

The present invention further provides automation features which include a feed hopper that will store a large supply of cigarettes to be fed automatically and consecutively to be advanced for smoking and testing. Numerous individual measurements on a batch of cigarettes may thus be carried out under uniform conditions free from variables that might otherwise be introduced due to operator influence. The apparatus of the present invention has a self-zeroing feature which includes both a measuring foot and a reference foot which are automatically disposed in a self-zeroing relationship against a cigarette under test. The firmness is determined by the difference in the depth to which the measuring foot deflects the wrapper beyond where the reference foot has come to rest. A dead weight loading technique is employed to weight both reference foot and the measuring foot to minimize tendencies for erroneous readings which were introduced in prior art devices due to the use of balances which included balance beams pivoted on knife edges for support and which were therefore subject to errors in firmness readings by the presence of worn or defective knife edges.

DETAILED DESCRIPTION OF THE INVENTION

The method of the present invention uses a system wherein linear variable differential transformers (LVDTs) are used to measure the amount of deflection in a cigarette due to a given load at test points on a cigarette before and during smoking. The present invention also measures the lengths of the burning cigarette at a given time during the smoking process so that the degree of firmness taken at that time may be related to the length smoked. An infrared scanner travels along the axis of the cigarette to seek out and record the position of the burning coal and detects and signals its position to thereby detect butt length.

The apparatus is fully automatic in its functions. A feed hopper 32 (FIG. 2) is loaded with a number of cigarettes 30, which are fed sequentially be means of an insertion unit 110 including a plunger unit 34 one at a time for testing the cigarette being inserted in mouthpiece 38 of a holder mounted on a rotary turntable 42. Signals generated by the LVDTs and infrared scanner are manipulated electronically to result in values of rod firmness for given lengths of rod smoked and are displayed digitally and data are automatically printed out in the manner described below.

Figure 1:
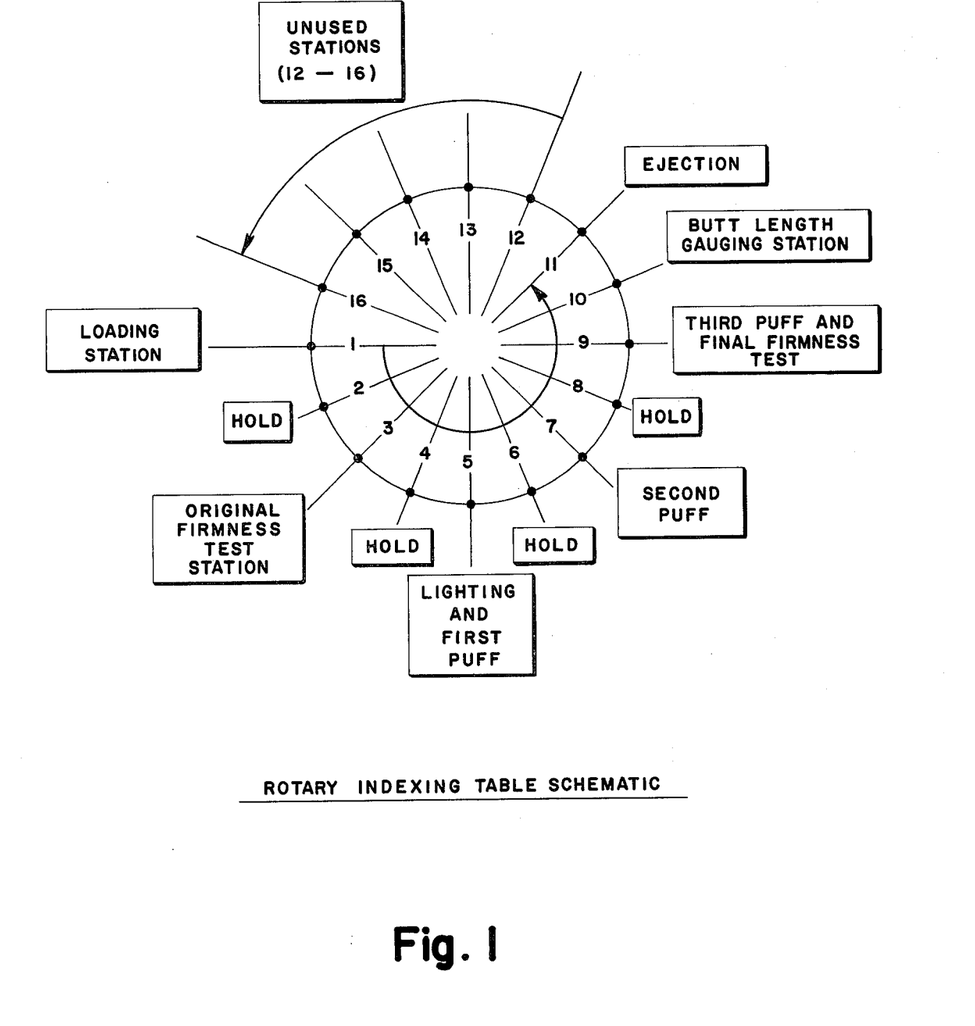
FIG. 1 is a block diagram of indexing table functions.

In FIG. 1 is shown a box diagram plan view of radially arranged numbered testing station positions representative of the several and successive positions of rest and function to which the turntable is rotated stepwise, the turntable being driven intermittently at timed intervals by a geneva motion drive device or other suitable stepping drive device (not shown). The testing stations shown are numbered 1 through 16 with Stations 1-11 having their respective functions noted in adjoining boxes, Stations 12-16 being unused. At Station 1 a cigarette 30 is loaded into the mouthpiece of a holder 114 and is held in place for a preset interval of time pending movement to Station 2 on passage of an interval of time that has been preset into a command unit (not shown) for advancing and sequentially positioning test cigarettes at the several successive test positions 1 through 11. These functions in sequence are described as follows:

On reaching Station 3, an initial firmness reading is taken by the apparatus and a signal generated by the reference and test foot LVDTs and transmitted electronically into a memory storage section. At the next position at Station 4, no function is performed on the cigarette—it merely waits through the timed cycle to advance to Station 5 for lighting.

At Station 5 the cigarette is lit and a first puff taken while connected to smoking machine puffing apparatus (FIG. 5) through the duct 5a, through a filter 5b into the port 5c which is lowered into sealing relationship with the filter port 5g, and a first puff is drawn through the opening 5e of port 5c and through the tubing 5d which is connected to a puffing machine of known construction. At Station 6 the cigarette is allowed to burn quiescently. After advancing to Station 7, the cigarette is puffed a second time by the mechanical puffing machine. At Station 8 the cigarette is allowed to burn quiescently. After advancing to Station 9, the cigarette is puffed once again while a final firmness test is taken. At the end of the preset timed interval, the test cigarette is advanced to Station 10 where an infrared scanning device traverses the burn path to reach the position of the burning coal. On intercept, the infrared device detects and records the position of the burning coal. A signal generated at the intercept point is translated electronically into a value for the length of cigarette remaining or smoked. The signal is then advanced for storage in a memory unit, displayed on a digital device, and/or printed out by a printer adapted for the purpose. The values for firmness and cigarette length for each successive sample are then printed out in the columnar arrangement shown in Tables 1 and 2, infra.

Figure 2:
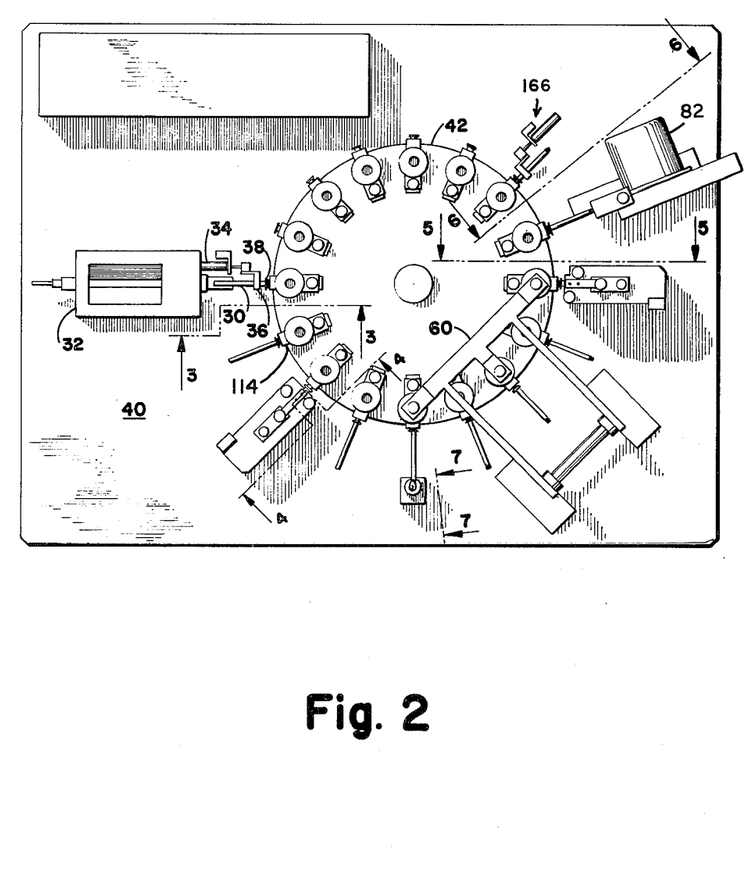
FIG. 2 is a plan view of the apparatus of the invention.

Now referring to FIG. 2, such figure shows the apparatus of the present invention in plan view with the same orientation of test positions as shown in the schematic diagram of FIG. 1 with a cigarette 30 shown as being loaded at position 1. Extending counter clockwise from position 1, each test station will be referred to by number as marked in FIG. 1.

Figure 3:
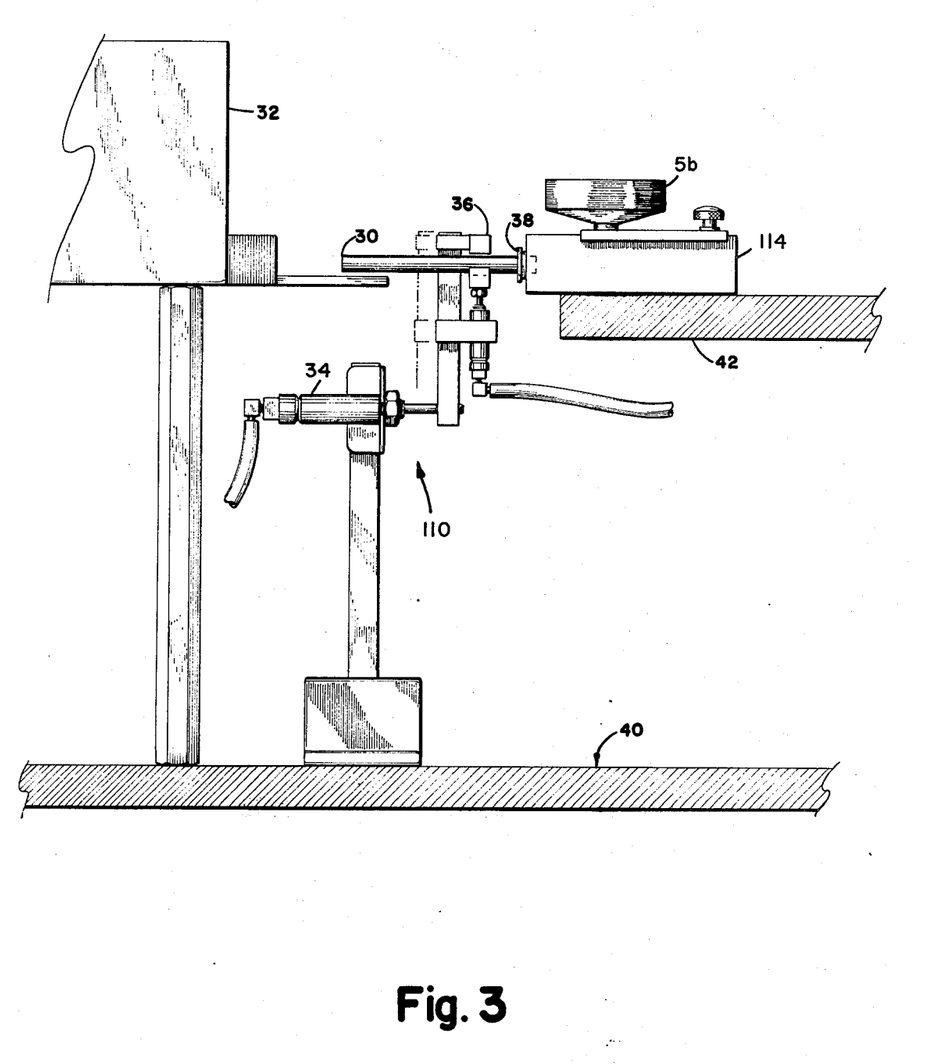
FIG. 3 is a view partly in section taken on line 3—3 of FIG. 2.
Figure 4:
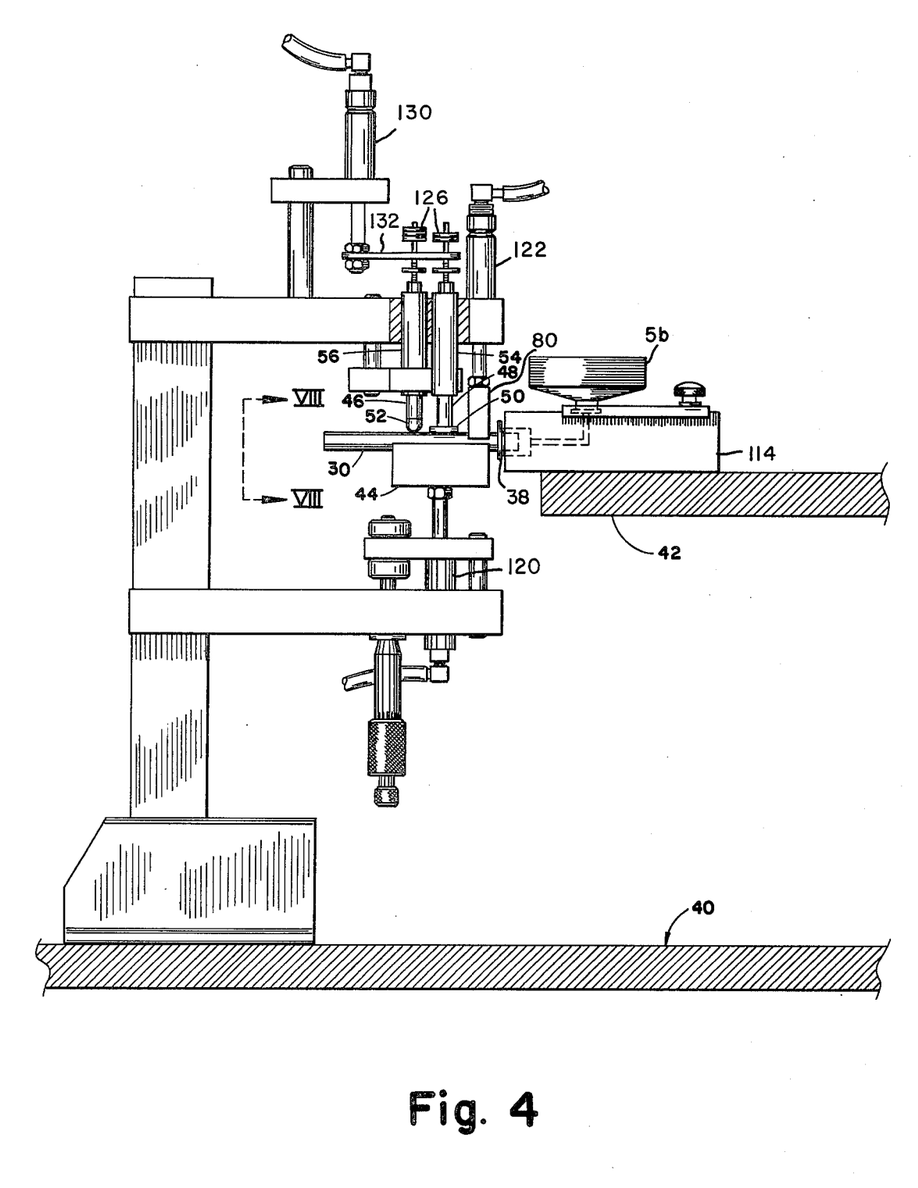
FIG. 4 is a view partly in section taken on line 4—4 of FIG. 2.
Figure 5:
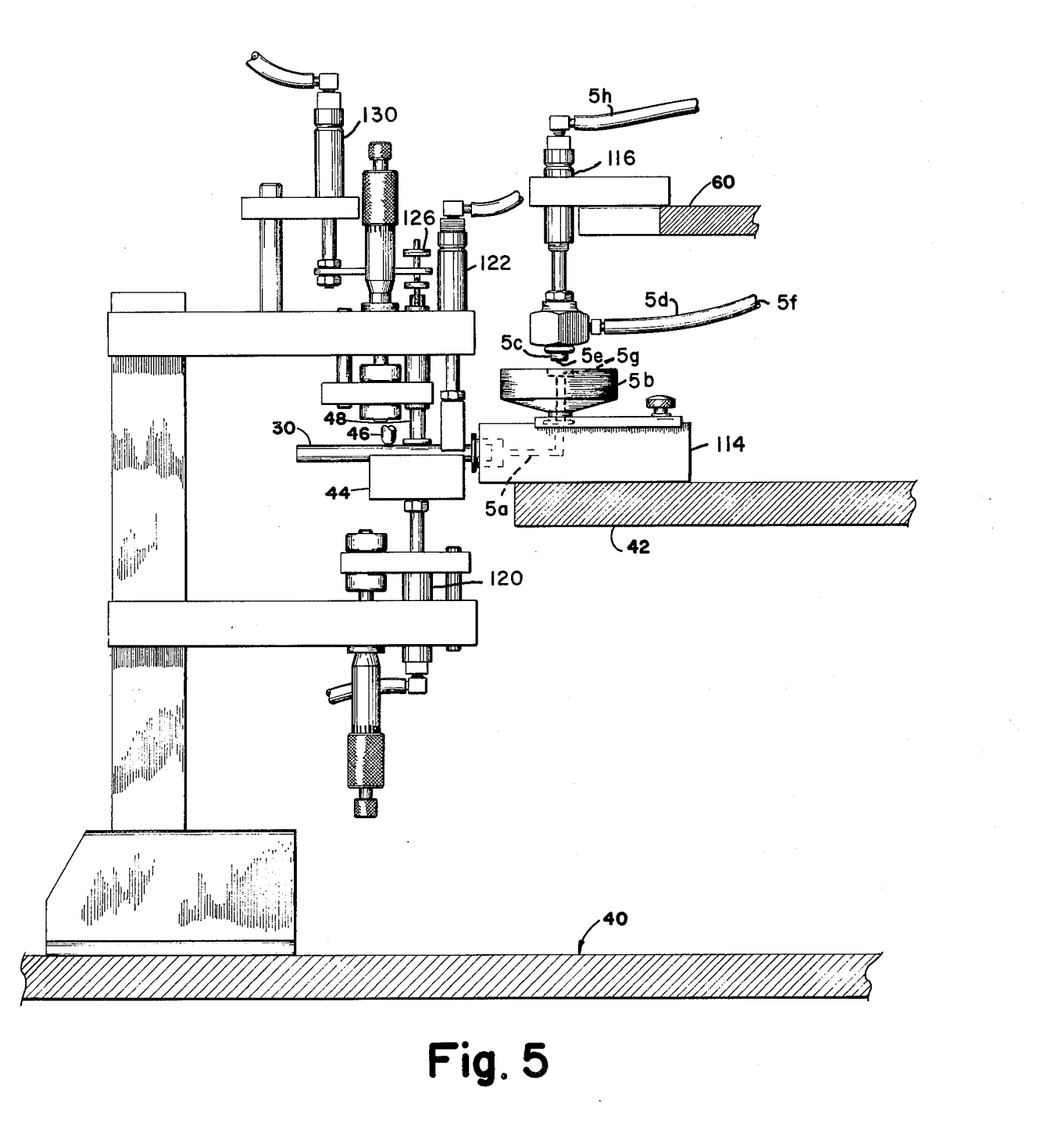
FIG. 5 is a view partly in section taken on line 5—5 of FIG. 2.

Referring again to FIG. 2, a cigarette 30 is shown in place at Station 1 after being pushed from the bottom of the hopper 32 by plunger 34 (shown in extended position full lines in FIG. 3) and grasped by a fork 36, which then inserts the cigarette 30 into the mouthpiece attachment 38 of holder 114 that is adapted for communication connection by filter 5a to a smoking machine puffing apparatus (not shown) smoke being piped to assembly 60 of FIG. 5 through the hollow tubing 5d. The total assembly 60 is provided with suitable mechanism to bring the port 5c into sealing contact with the filter 5b at the port 5g. On reaching registration, the air cylinder 116 is actuated by air from tubing 5h and port 5c is brought into sealing relationship with port 5g in the filter 5b. A puff can be taken and the assembly then raised to allow the turntable 42 to be rotated to the next position. After a timed short wait, the turntable 42 (mounted on apparatus base 40), on which the cigarette holders 114 are located, indexes to bring the unlit cigarette to the next consecutive station at position 2. After a short timed interval, the turntable 42 is indexed to position the cigarette at position 3 (FIG. 1) by means of a stepping or indexing apparatus (not shown) which is adopted to drive the turntable 42 through the successive changes of position. A cigarette rest 44 is then raised under the cigarette 30 by means of cylinder unit 120 and upper V-block 80 is lowered by cylinder unit 122 for supporting the cigarette and sensing feet 46 and 48 are lowered onto the cigarette. The sensing feet each are rod-shaped units having lower cigarette contacting ends and are arranged parallel one with the other, being slidably received in sleeve type LVDT units 56, 54 respectively. The sensing feet are weight activated, i.e., the upper ends are fitted with weight 126 to provide that when cylinder 130 strokes downwardly, arm 132 fixed thereto releases the rods to allow them to free fall concurrently by gravity to transmit deflection forces to the cigarette when they contact same. By stroking cylinder 130 to raise arm 132, the rods are retracted away from the cigarette. Reference foot 48, which is designed to be of minimum weight, is made with a flat disc 50 at its lower end that lies on the wrapper of cigarette 30 and the cylinder of tobacco encircled by the wrapper and senses to establish a reference level to which can be related the depth of sink of measuring foot 46 to thereby provide a firmness value. Foot 46 is more heavily weighted than foot 48 and has a rounded end 52 for better deflection of the wrapper of cigarette 30. After the cigarette 30 is subjected to the weight of the sensing feet for a given time, the electrical output of the LVDTs 54 and 56 (which function as signal producing devices indicative of the deflection produced in the cigarette), which then has bottomed at the relative amount of deflection of the measuring foot 46 in comparison to the reference foot 48, is electronically frozen and entered into a memory section of the micro computer of FIG. 9. The sensing feet 46 and 48 and cigarette rest 44 and V-block 80 are then retracted and the cigarette is advanced to the next Station 4.

The cigarette support area 58 in the cigarette rest 44 and that 81 of the upper V-block are in the juxtaposed faces of this block set made in a "V" shape to receive and embrace the cigarette 30 and align it to ensure that the cigarette is centrally located axially so the sensing feet 46 and 48 may intercept the cigarette 30 properly along its axis and also to support a substantial length of the cigarette while the deflection forces are being applied thereto. The reference foot 48 is made with a flat surface, i.e., is provided with a disc 50 at the cigarette contacting end and is made of a light weight material so that it does not unduly deform the cigarette. In this position, therefore, it can be used to establish a reference position against which the penetration of the cigarette 30 by measuring foot 46, which is rounded or hemispherically tipped at its cigarette contacting end is loaded with a greater magnitude of weight than the weight applied to the reference foot, can be measured to be translated into a value for firmness by the electronics of the control equipment.

A firmness number is derived by determining the difference in the output signals of the linear variable displacement transformers (LVDTs), one of which is associated with each of the sensing feet 46 and 48. This results in a self-zeroing arrangement in that the referencing foot 48 finds its own level and depth of penetration of measuring foot 46 is taken in relation to the position of the level of referencing foot 48. LVDT output can be manipulated electronically so that the difference in depth of penetration may be read out of the control equipment in any desired units such as millimeters.

Figure 7:
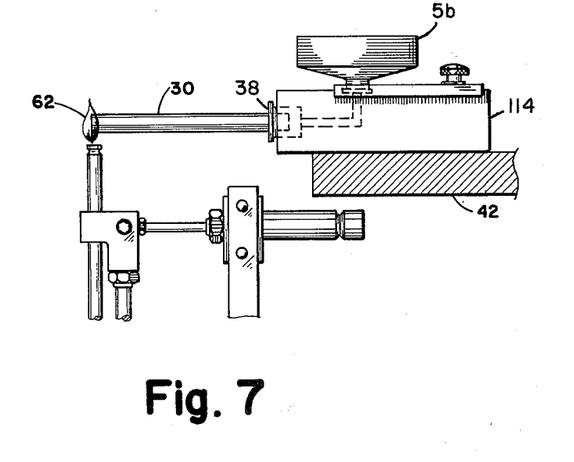
FIG. 7 is a view partly in section taken on line 7—7 of FIG. 2.
Figure 8:
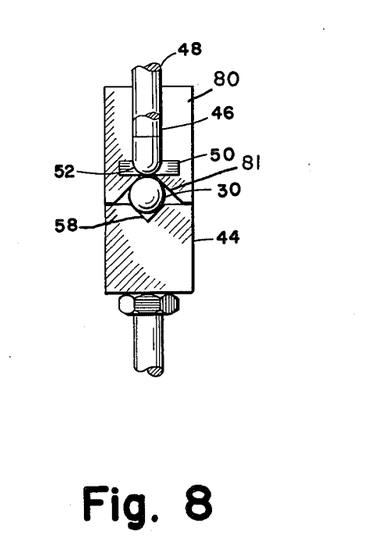
FIG. 8 is a view taken on line VIII—VIII of FIG. 4.

The cigarette 30 is held at position or station 4, and after a short wait advanced to the following position 5. Once in place at position 5, interconnection to the smoking machine puffing apparatus is made by the lowering of the assembly mounted on the connector bar 60 (see FIG. 5). A flame source 62 (FIG. 7) is then brought to lie adjacent the cigarette end to ignite same, and a lighting puff is taken on the cigarette by the aforementioned puffing machanism. All smoking of the cigarette can be done in the puffing mechanism by, e.g., a syringe-type smoking machine, which takes a 35 cc puff in 2 seconds.

After lighting, the cigarette 30 is indexed to the next position 6, and after a short wait is advanced to position 7. Here again a connection is made to the puffing mechanism of the smoking machine and a second puff is taken. The cigarette 30 is then indexed to the next position 8, and after a short wait is moved to position 9. Connection to the smoking machine is again made and a "V"-block cigarette rest 44 is raised and upper V-block 80 is lowered to support the cigarette 30 and to keep it centralized while a second set of sensing feet 46 and 48, such as shown and described for test position 3, are used to take a final firmness reading at Station 9. The cigarette support 44 and upper V-block 80 are made of a thermally insulating material to prevent condensation from forming at the cigarette interface. The flat reference foot 48 and the tip of the hemispherical masuring foot 46 are also made of insulating material to prevent condensation. A short time before the last puff is taken, the sensing feet are lowered onto the cigarette. After the last puff is taken by the smoking machine, the electronic readout from the LVDTs at the position is frozen and the sensing feet and "V"-blocks are retracted.

Figure 6:
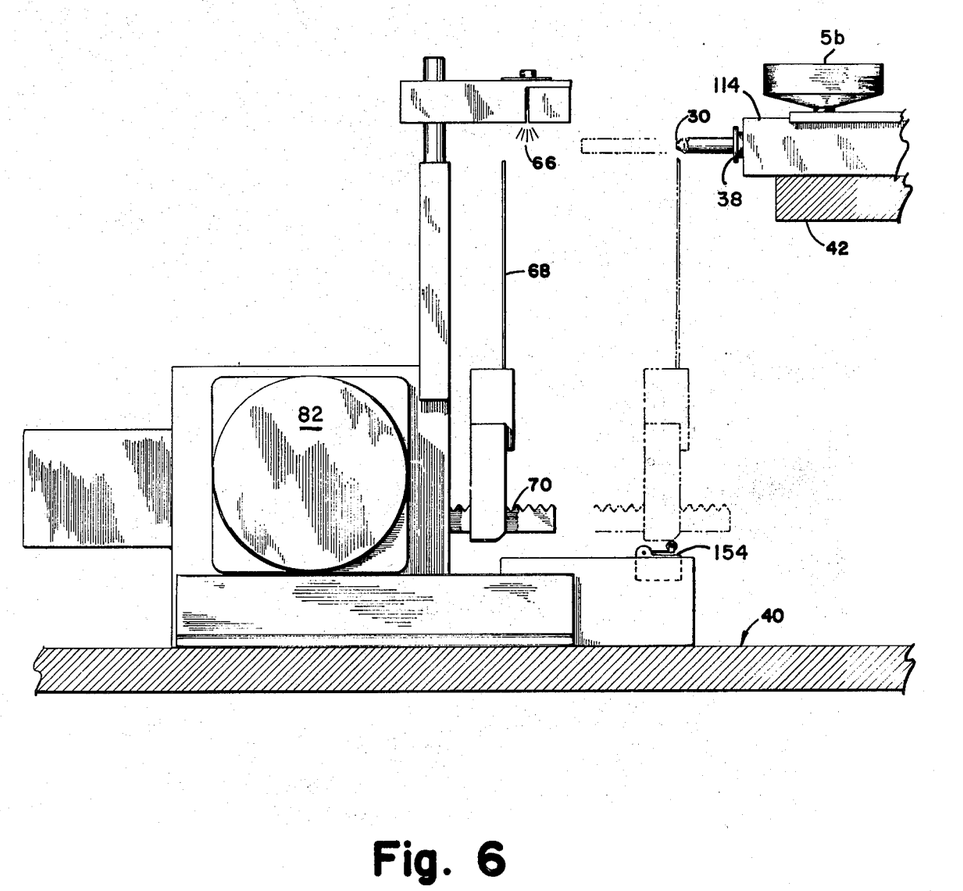
FIG. 6 is a view partly in section taken on line 6—6 of FIG. 2.

The cigarette 30 is then indexed to the next position or station 10. The infrared length measuring device of FIG. 6 is then automatically activated. This device consists of an infrared detector 68 mounted on a rack 70 driven by a stepping motor 82, which drives the detector 68 codirectionally along the axis of the path of the burning coal. When triggered, the infrared scanner travels from light reference 66 toward the holder 114 until the hot coal of the cigarette is reached and detects the position of the cigarette coal in relation to preset fixed reference 66. On detecting the position of the burning coal, the scanner then reverses direction and returns to its original position, a limit switch unit 154 being employed to signal the control unit to prevent rack overrun.

A microprocessor counts the steps taken by the stepping motor in returning from the position of the coal the fixed light reference near the start position where it is inactivated. These steps as counted are then subtracted from the total steps required to travel to the preset fixed reference, the position of the cigarette tip. This number of steps is then converted into millimeters of butt length or length of cigarette smoked and entered into the memory unity. The cigarette butt is then indexed to the next station, position 11, where it is ejected from the holder 114 by means of ejection device 166.

Figure 9:
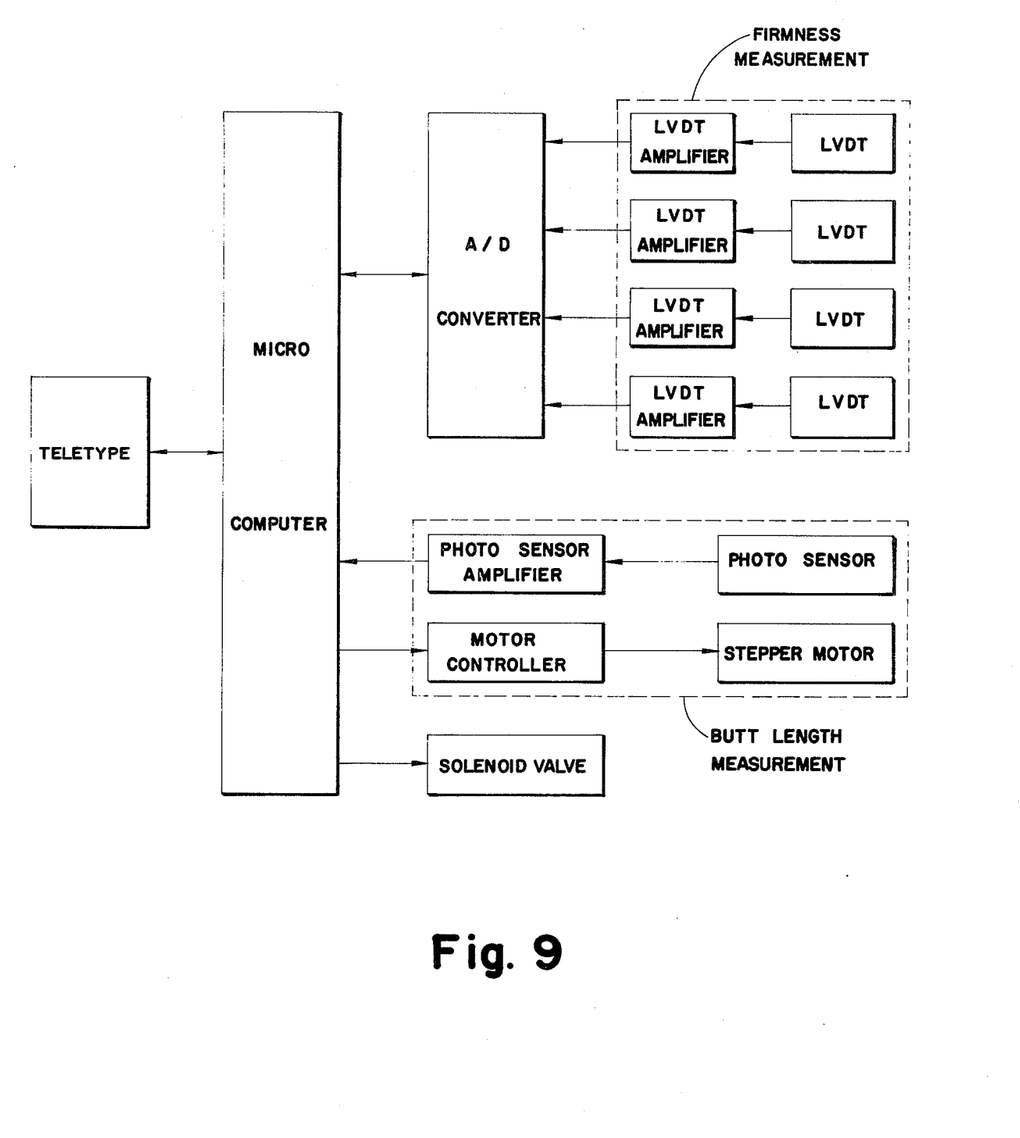
FIG. 9 is a block diagram depicting the electric and electronic functions of the associated control mechanisms.

FIG. 9 of the drawings shows a block diagram of the control functions that are incorporated in electronic apparatus (not shown) that are adapted to read signals emitted by the separate LVDTs which are mechanically connected to the reference and measuring feet at successive testing stations and of the photo sensor which is used in detecting and signalling butt length by detecting the position of the burning coal.

The LVDTs in the firmness measurement section convert the relative position of the sensing feet into a voltage reading. The voltage thus generated is then amplified by the connected LVDT amplifier and fed to the A/D converter which converts the voltage into a digital signal which then is fed into a micro computer. The digital signal is then manipulated within the micro computer in accordance with a preset program to convert the signal into a firmness value number and fed to the teletype unit where the firmness value is printed out on a sheet of paper.

In the butt length measurement section, the signal from the photo sensor is amplified and fed into the micro computer to instruct the micro computer as to the position of the coal and the length of butt measured at that position. The micro computer in turn computes and relays to the motor controller an instruction for the initiation and limitation of the length of travel and direction of the stepping motor in controlling the travel of the infrared scanner.

A solenoid valve is activated on command of the program as provided in the micro computer to coordinate puff action for smoking of the cigarette under test at the proper intervals and at the proper test station.

The end results of the electronic manipulation which take place in the control and data processing mechanism are printed out by the teletype unit as shown in the following Tables 1 and 2.

TABLE I

| SAMPLE | Blend A | | |
|---|---|---|---|
| | BUTT LENGTH | STATIC FIRMNESS | SMOKING FIRMNESS |
| 1 | 62.1 | .67 | 1.65 |
| 2 | 62.7 | .71 | 1.20 |
| 3 | 62.1 | .85 | 1.60 |
| 4 | 56.9 | 1.00 | 1.88 |
| 5 | 63.5 | 1.02 | 1.79 |
| 6 | 61.6 | .75 | 1.73 |
| 7 | 62.9 | .76 | 1.36 |
| 8 | 58.5 | 1.22 | 1.82 |
| 9 | 59.7 | .80 | 1.89 |
| 10 | 60.9 | .89 | 1.53 |

TABLE I-continued

| | Blend A | | |
|---|---|---|---|
| SAMPLE | BUTT LENGTH | STATIC FIRMNESS | SMOKING FIRMNESS |
| 11 | 65.4 | .70 | .96 |
| 12 | 63.5 | 1.06 | .94 |
| 13 | 60.5 | 1.02 | 1.84 |
| 14 | 56.6 | .86 | 2.03 |
| 15 | 64.5 | .75 | 1.89 |
| 16 | 63.7 | .61 | 1.62 |
| 17 | 63.2 | .69 | 1.09 |
| 18 | 62.9 | .91 | 1.50 |
| 19 | 59.2 | .85 | 1.37 |
| 20 | 62.2 | 1.22 | 2.06 |
| 21 | 61.4 | .74 | 1.50 |
| 22 | 59.8 | .85 | 1.59 |
| 23 | 58.2 | .78 | 1.88 |
| 24 | 61.6 | .82 | 1.28 |
| MEAN | 61.4 | .86 | 1.58 |
| STD. DEV. | 2.32 | .163 | 0.32 |

TABLE 2

| | Blend B | | |
|---|---|---|---|
| SAMPLE | BUTT LENGTH | STATIC FIRMNESS | SMOKING FIRMNESS |
| 1 | 59.8 | .61 | .64 |
| 2 | 63.3 | .66 | 1.50 |
| 3 | 65.3 | .61 | 1.24 |
| 4 | 64.6 | .57 | .74 |
| 5 | 61.9 | .48 | 1.41 |
| 6 | 62.9 | .62 | 1.70 |
| 7 | 64.6 | .58 | .57 |
| 8 | 65.4 | .62 | .46 |
| 9 | 63.0 | .74 | 1.14 |
| 10 | 63.5 | .89 | 1.79 |
| 11 | 61.4 | .48 | 1.23 |
| 12 | 60.5 | .44 | 1.37 |
| 13 | 66.7 | .59 | .71 |
| 14 | 63.5 | .38 | .68 |
| 15 | 61.6 | .55 | 1.10 |
| 16 | 62.4 | .56 | .52 |
| 17 | 58.7 | .67 | 1.56 |
| 18 | 63.0 | .65 | 1.14 |
| 19 | 64.3 | .57 | .77 |
| 20 | 64.0 | .28 | 1.28 |
| 21 | 62.9 | .47 | 1.40 |
| 22 | 62.1 | .61 | 1.45 |
| 23 | 65.7 | .27 | .44 |
| 24 | 64.5 | .48 | .61 |
| MEAN | 63.2 | 0.56 | 1.06 |
| STD. DEV. | 1.91 | 0.14 | 0.42 |

These data represent twenty-four cigarettes of Blend A and twenty-four of Blend B. Statistical analysis of these results shows Blend A is softer both before and during smoking than Blend B. Blend A is also shown to be shorter than Blend B on average.

What is claimed is:

1. Apparatus for measuring the firmness of a cigarette comprised of a paper wrapped cylinder of tobacco during the smoking of same, said apparatus comprising
a holder for receiving the cigarette,
means for advancing said holder in stepwise movement to a succession of stations,
means for igniting and then effecting puffing of said cigarette at one of said stations, and
means located at a succeeding one of said stations for concurrently applying a first reference magnitude deflection force to said cigarette and a second greater magnitude deflection force to said cigarette, said means including signal generating devices associated with the application of the respective deflection forces for producing signals indicative of the extent to which the respective forces have deflected the wrapper.

2. The apparatus of claim 1 further comprising means for effecting further puffing of said cigarette at a station intervening said one station and said succeeding station.

3. The apparatus of claim 1 further comprising means for effecting further puffing of said cigarette at said succeeding station.

4. The apparatus of claim 1 in which the deflection force applying means comprises a pair of rods reciprocally slidable along parallel courses and force inducing devices associated with each rod operative to slide the respective rods with unequal magnitude of force in one direction into contact with said cigarette, there being a retraction device engageable with said rods for sliding same in an opposite direction out of contact with said cigarette.

5. The apparatus of claim 4 further comprising support means for supporting a substantial length of the cigarette to maintain the longitudinal axis of same perpendicular to the sliding courses of said rods while said cigarette is disposed at said one station and at least during the time said rods are in deflective force applying contact therewith.

6. The apparatus of claim 4 in which said holder holds said cigarette in a disposition wherein its longitudinal axis is in a horizontal orientation, said pair of rods being disposed in a vertical orientation, the force inducing means associated with said rods comprising weights connected to the ends of said rods opposite the cigarette contacting ends thereof, there being a lesser quantum of weights connected to said first rod than to said second rod, said retraction device being movable to a rod nonengaging position to release said rods for gravity sliding of same in the direction of said cigarette.

7. The apparatus of claim 6 in which the cigarette contacting end of said first rod has a flat disc-shaped member fixed thereto, the cigarette contacting end of said second rod being of rounded contour.

8. The apparatus of claim 4 in which said signal generating devices are linear variable differential transformers.

9. The apparatus of claim 8 in which said transformers are of sleeve configuration, said rods being slidably received in said sleeves.

10. The apparatus of claim 5 in which the cigarette support means comprises a block set movable together to bring juxtaposed faces thereof in supportive embrace about said cigarette.

11. The apparatus of claim 10 in which the juxtaposed faces of said block set are provided with cigarette receptive V-notches.

12. The apparatus of claim 5 in which the cigarette contacting ends of said rods and said cigarette support means are of thermally insulating material.

13. The apparatus of claim 1 further comprising means located at a station next following said succeeding one of said stations for detecting the location of the burning coal of the cigarette relative to a fixed reference location to therewith determine the length of said cigarette smoked.

14. The apparatus of claim 13 in which said detecting means includes an infrared detector, a mounting for said infrared detector, and means connected with said mounting for moving same fraom said reference location codirectionally of the axis of said cigarette toward said burning coal, said means being operable to return said mounting to said fixed reference location following detection of the location of said burning coal.

15. The apparatus of claim 1 further including deflection force applying means located at a station preceding said one station for measuring the firmness of the cigarette prior to smoking of same, such means being effective to apply a first reference magnitude deflection force to said cigarette and a second greater magnitude deflection force to said cigarette, such means having associated therewith signal generating devices associated therewith signal generating devices associated with the application of the respective deflection forces for producing signals indicative of the extent to which the respective forces have deflected the wrapper.

16. The apparatus of claim 1 in which the holder advancing means comprises a rotary turntable on which the holder is mounted, the stations being circularly spaced around the travel path of said turntable, said turntable being indexable stepwise to the successive ones of said stations.

17. The apparatus of claim 16 in which the stations include an initial cigarette loading station, there being a stock of cigarettes at said initial station, and means for transferring a cigarette from said stock to said holder.

18. The apparatus of claim 17 further comprising ejection means for ejecting a smoked cigarette from said holder at a station subsequent to said succeeding one of said stations.

19. A method for measuring the firmness of a cigarette comprised of a paper wrapped cylinder of tobacco during the smoking of same, said method comprising igniting the cigarette and puffing same a predetermined number of times, then concurrently applying a first reference magnitude of deflection force to said cigarette and a second greater magnitude, deflection force to said cigarette, and recording the differential of wrapper deflection produced by the respective forces to provide a firmness value.

20. The method of claim 19 in which the deflection forces are applied to said cigarette substantially perpendicularly to the longitudinal axis of the cigarette and at closely spaced locations along the length of the cigarette.

21. The method of claim 19 comprising holding the cigarette with its axis in a horizontal attitude, and applying said deflection forces along vertically oriented courses.

22. The method of claim 21 in which said deflection forces are free-fall weight induced forces.

23. The method of claim 20 further comprising supporting a substantial length of the cigarette at least during the time said deflection forces are being applied thereto.

24. The method of claim 19 further comprising sensing the location of the burning coal on said cigarette relative to a reference location following the application of the deflection forces thereto.

25. The method of claim 24 in which the burning coal location is sensed by infrared detection.

* * * * *